United States Patent
Chen et al.

(10) Patent No.: US 11,959,160 B2
(45) Date of Patent: Apr. 16, 2024

(54) COPPER-NIOBIUM ALLOY FOR MEDICAL BIOPSY PUNCTURE NEEDLE

(71) Applicant: University of Shanghai for Science and Technology, Shanghai (CN)

(72) Inventors: Xiaohong Chen, Shanghai (CN); Xiaofei Liang, Shanghai (CN); Honglei Zhou, Shanghai (CN); Jian Zhao, Shanghai (CN); Ping Liu, Shanghai (CN); Shaoli Fu, Shanghai (CN)

(73) Assignee: University of Shanghai for Science and Technology, Shanghai (CN)

( * ) Notice: Subject to any disclaimer, the term of this patent is extended or adjusted under 35 U.S.C. 154(b) by 0 days.

(21) Appl. No.: 17/861,105

(22) Filed: Jul. 8, 2022

(65) Prior Publication Data

US 2023/0043705 A1 Feb. 9, 2023

(30) Foreign Application Priority Data

Jul. 13, 2021 (CN) .......................... 202110791896.X

(51) Int. Cl.
  *C22C 9/00* (2006.01)
  *A61B 10/02* (2006.01)

(52) U.S. Cl.
  CPC ............ *C22C 9/00* (2013.01); *A61B 10/0266* (2013.01)

(58) Field of Classification Search
  CPC . A61B 10/02; A61B 10/0233; A61B 10/0241; A61B 10/025; A61B 10/0266; A61B 10/0275; A61B 10/0283; A61B 10/0291; A61B 2010/0208; A61B 2010/0225; A61B 2010/0258;

(Continued)

(56) References Cited

U.S. PATENT DOCUMENTS

2019/0192124 A1* 6/2019 Park .................. A61M 25/0043
2020/0029942 A1* 1/2020 Shang ................. A61B 5/6848

FOREIGN PATENT DOCUMENTS

CN 101225486 A 7/2008
CN 106676313 A 5/2017

(Continued)

OTHER PUBLICATIONS

Ren, Y. et al. "A Review: Research on MR-Compatible Alloys in MRI", Acta Metallurgica Sinica, vol. 53, Issue 10, pp. 1323-1330, Oct. 2017.

(Continued)

*Primary Examiner* — Brian D Walck
*Assistant Examiner* — Nazmun Nahar Shams
(74) *Attorney, Agent, or Firm* — Bochner PLLC; Andrew D. Bochner

(57) ABSTRACT

Disclosed is a copper-niobium alloy for a medical biopsy puncture needle. A needle core and/or needle tube of the puncture needle are/is made of the copper-niobium alloy. The copper-chromium alloy includes the following components by mass: 5≤Nb≤15 and the balance of Cu. A copper alloy with designed components is obtained by combining a diamagnetic material Cu with paramagnetic Nb, and compared with existing medical stainless steel and titanium alloy, the copper alloy has greatly reduced magnetic susceptibility, and specifically, the artifact area and volume are also significantly reduced. In addition, the blank of use of the copper alloy in medical biopsy paracentesis is filled.

2 Claims, 3 Drawing Sheets

(58) Field of Classification Search
CPC ............ A61B 2010/045; C22C 1/0425; C22C 45/001; C22C 9/00; B22F 2301/10
See application file for complete search history.

(56) References Cited

FOREIGN PATENT DOCUMENTS

| | | | | |
|---|---|---|---|---|
| CN | 109009425 A | * | 12/2018 | ......... A61B 10/0233 |
| JP | 2000243139 A | * | 9/2000 | ............... A61K 6/15 |
| WO | WO-2022257915 A1 | * | 12/2022 | ............... A61K 6/15 |

OTHER PUBLICATIONS

First Office Action of the China National Intellectual Property Administration (CNIPA) dated Feb. 21, 2022, in related Chinese Appl. No. 202110791896.X, 13 pages.

* cited by examiner

COPPER-NIOBIUM ALLOY FOR MEDICAL BIOPSY PUNCTURE NEEDLE

CROSS REFERENCE TO RELATED APPLICATION

This patent application claims the benefit and priority of Chinese Patent Application No. 202110791896.X, filed on Jul. 13, 2021, the disclosure of which is incorporated by reference herein in its entirety as part of the present application.

TECHNICAL FIELD

The present disclosure belongs to the field of medical devices, and mainly relates to the technical field of tissue puncture such as lumbar puncture in biopsy operation and extraction of bone marrow fluid in bone marrow puncture operation, and in particular, to a use of a copper-niobium alloy in a biopsy puncture needle.

BACKGROUND ART

In recent years, with the development of magnetic resonance imaging (MRI) detection technology and equipment, MRI plays an important role in medical fields such as diagnostics and radiology, and has been widely used in orthopedics and neurosurgery. MRI has superior soft tissue contrast compared with traditional imaging techniques such as X-ray photography and computed tomography (CT), is not affected by ionizing radiation, and can acquire information on any plane through three-dimensional (3D) imaging.

However, the external magnetic field resonates with the magnetic metal in magnetic resonance. Since the 316L medical austenitic stainless steel and titanium alloy currently used in clinical practice have certain magnetic properties, magnetic field disturbance is caused during MRI detection. Therefore, during surgical diagnosis, the output image is turbulent due to the instability of the magnetic field, resulting in some blurred areas, which are defined as magnetic susceptibility artifacts. The artifacts will interfere with intraoperative treatment and postoperative diagnosis, and even cause misjudgment of the operation in severe cases, which will adversely affect doctors and patients. Therefore, it is particularly important to develop alloys with low magnetic susceptibility. From the perspective of reducing the magnetic susceptibility difference between the metals and human tissues, and combined with the consideration of alloy materials for puncture needles in the Chinese market, it is finally found that copper alloys have a certain value in reducing the magnetic susceptibility of metals through screening. The Institute of Metal Research, Chinese Academy of Sciences has reported on silicon brass. However, the research on the application of copper alloys in MRI is still in the early stage.

After solid solution, large deformation, and aging, the toughness of the binary copper alloy obtained by combining Nb with the copper matrix decreases and the strength increases sharply. Nb itself has good biocompatibility, and human tissues grow in the network structure made of niobium wire.

SUMMARY

In order to reduce the artifact problem of medical alloys in biopsy puncture, the present disclosure provides a Cu—Nb alloy with lower magnetic susceptibility and a preparation method thereof. By combining diamagnetic Cu with a paramagnetic material Nb, the magnetic susceptibility and the artifact area are reduced.

The present disclosure mainly aims at developing a material that can reduce the artifact area and volume and has certain strength and biocompatibility and low cytotoxicity in the presence of the unavoidable artifacts in medical images in biopsy puncture. A copper matrix is combined with a metal element with excellent performance and weak magnetic properties, and mechanical properties of the alloy are improved through a large-deformation manufacturing process, so as to explore the breakthrough of the copper alloy in biopsy puncture.

A technical solution used by the present disclosure includes:

A use of a copper-niobium alloy in a medical biopsy puncture needle is provided. The copper-niobium alloy is used as a material for a needle core and/or needle tube of the puncture needle, and the copper-niobium alloy includes the following components by mass: $5 \leq Nb \leq 15$ and the balance of Cu.

The needle core and the needle tube are processed as follows:

(1) using granular materials with a purity greater than or equal to 99.99% for smelting to obtain a copper-niobium alloy ingot with a diameter of 60-100 mm, where through particle suspension smelting, the smelted component is uniform;

(2) cutting off a riser and finishing a surface of the ingot;

(3) placing the ingot in a high temperature furnace for heat treatment at 900-1,000° C. for 1-2 h, and forging the ingot to a round bar with a diameter of 10-30 mm;

(4) conducting solution quenching treatment on the round bar at 900-1,000° C. for 2-4 h; and (5) conducting needle core forming: drawing the round bar processed in step (4) in multiple passes to the needle core of a design specification, and conducting annealing at 550-650° C. for 1-2 h; and conducting needle tube forming: drilling the round bar processed in step (4), and conducting continuous operations of tube reducing, continuous rolling, and heat treatment to finally obtain the needle tube of a design specification.

The determination of the percentage of element content in the alloy is based on the comprehensive consideration of the influence of mechanical properties and the uniformity of the structure. Since Nb and copper are almost not insoluble, and have quite different melting points, it is difficult to obtain compounds with uniform structural composition. In general, the Nb content should be maintained at the middle content ratio, which not only strengthens the alloy, but also avoids the nonuniform structural composition caused by the process. The finally determined preferred component is Cu10Nb, that is, the Nb content in the copper-niobium alloy is controlled at 10%.

According to the present disclosure, a copper alloy with designed components is obtained by combining a diamagnetic material Cu with paramagnetic Nb, and compared with existing medical stainless steel and titanium alloy, the copper alloy has greatly reduced magnetic susceptibility, and specifically, the artifact area and volume are also significantly reduced. In addition, the blank of use of the copper alloy in medical biopsy paracentesis is filled.

DETAILED DESCRIPTION OF THE EMBODIMENTS

The present disclosure is described in more detail below with examples that optimize and analyze the materials of the present disclosure.

Figure 1:
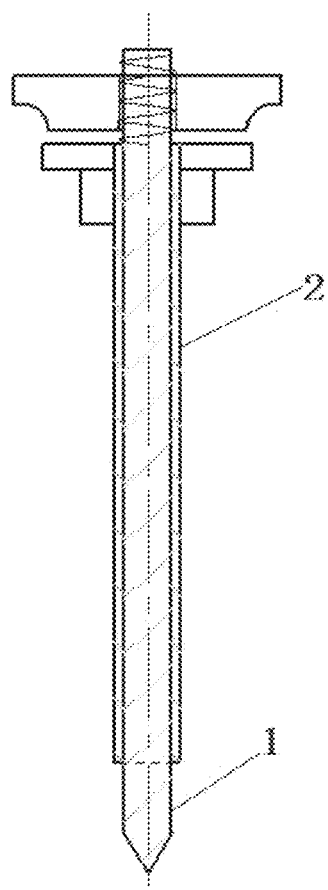
FIG. 1: a structure of a medical biopsy puncture needle.

FIG. 1 shows a basic structure of a conventional medical biopsy puncture needle, mainly including a needle core 1 and a needle tube 2. The needle core 1 is inserted into the needle tube 2 and can move up and down. In the puncture process of orthopedic operation, the needle tube are mainly used for positioning, and cooperates with the needle core to penetrate the bone marrow.

Taking the Cu10Nb alloy as an example below, specific processing of the medical biopsy puncture needle of the present disclosure is described in detail.

(1) Small particle raw materials with a purity greater than or equal to 99.99% (particle size of about 10 mm) were used for smelting to obtain Cu10Nb with a mass of 20 kg and a diameter of 80 mm.

(2) A riser was cut off and a surface of the ingot was finished.

(3) The ingot was placed in a chamber electric furnace for heat treatment at 960° C. for one hour, and the ingot was forged to a round bar with a diameter of 20 mm.

(4) Solution quenching treatment was conducted on the round bar at 960° C. for two hours.

(5) Needle core forming was conducted:

The round bar obtained in step (4) was drawn in multiple passes to needle cores with diameters of 3.61 mm, 3.5 mm, 2.65 mm, 2.2 mm, and 0.9 mm, and intermediate annealing was conducted at 600° C. for 1 h.

Figure 2:
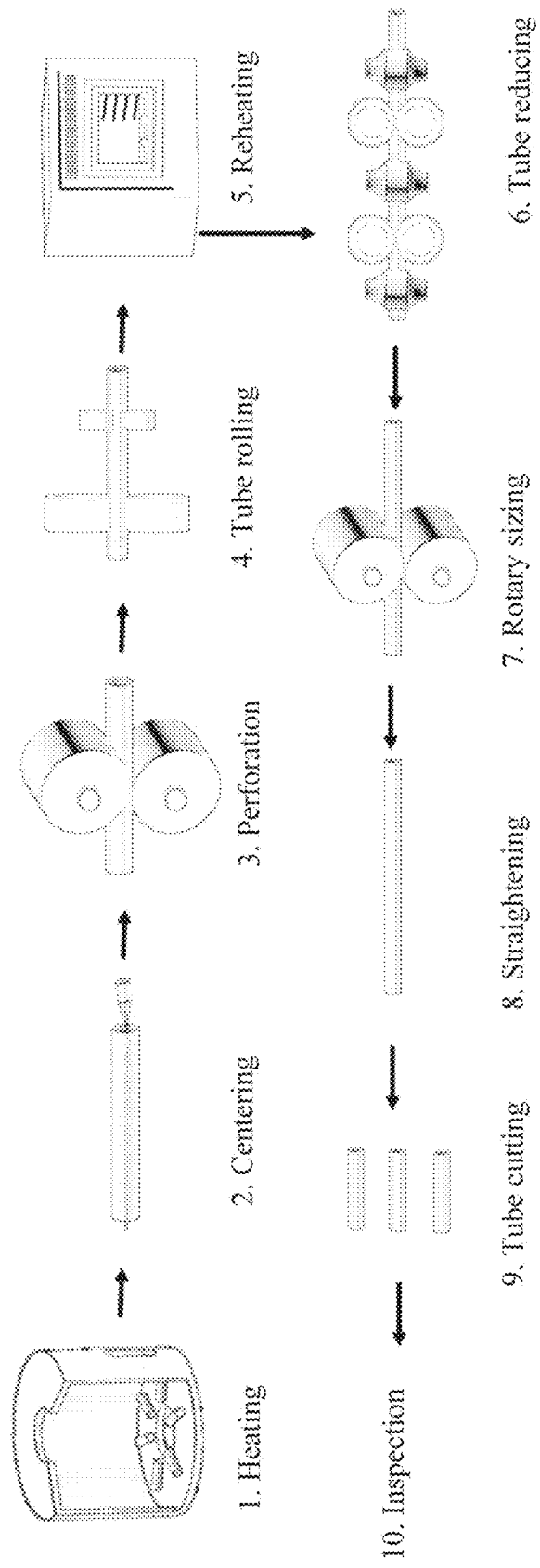
FIG. 2: a flow chart of needle tube processing.
Figure 3:
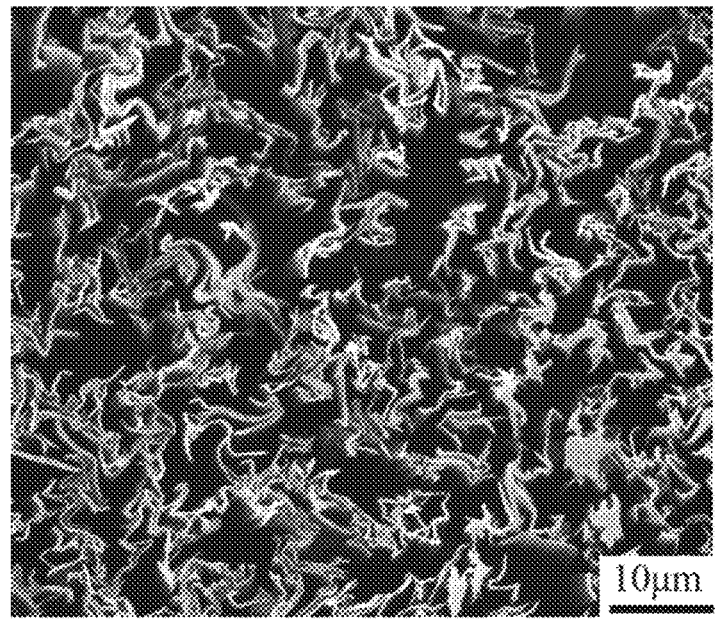
FIG. 3: a scanning electron image (SEM) of Cu10Nb with a diameter of 2.65 mm after large deformation.

Needle tube forming was conducted:

The round bar obtained in step (4) was drilled to obtain a tube with an aperture of 13 mm and an outer diameter of 20 mm, and continuous operations of tube reducing, continuous rolling, and heat treatment were conducted (see FIG. 2). The finally obtained size of the needle tube is shown in Table 1:

TABLE 1

Needle tube size

| Nominal outer diameter (mm) | Inner diameter (mm) | Wall thickness (mm) | Length (mm) |
|---|---|---|---|
| 1.4 ± 0.01 | 0.95 | 0.225 | 100 |
| 3.33 ± 0.01 | 2.33 | 0.5 | 100 |
| 3.5 ± 0.01 | 2.8 | 0.35 | 100 |
| 4.17 ± 0.01 | 3.61 | 0.28 | 100 |

Performance Test

I. Ion Precipitation Detection

In the present disclosure, the Cu10Nb alloy was compared with electrolytic Cu to detect the precipitation of Cu ions in the simulated body fluid, but the precipitation of Nb was not detected, so it is not listed in the table. The test results are shown in Table 2.

TABLE 2

Precipitation of Cu ions in simulated human body fluids (mg/L)

| Material | Cu-ion dissolution | | |
|---|---|---|---|
| | (7 days) | (15 days) | (30 days) |
| Cu | 4.81 | 8.58 | 10.09 |
| Cu10Nb | 3.49 | 5.90 | 7.83 |

II. Corrosion Resistance Testing

The present disclosure tested anodic polarization curves of Cu, Cu10Nb and a comparative material SUS304 in simulated body fluid. The results are shown in Table 3.

TABLE 3

Corrosion potential and corrosion current density of three materials in simulated human body fluids

| | Ecorr (V) | Icorr ($10^{-6}$ A/cm$^{-2}$) |
|---|---|---|
| Cu | −0.24 | 7.544 |
| Cu10Nb | −0.29 | 4.608 |
| SUS304 | −0.26 | 0.176 |

III. Magnetic Susceptibility Test

Hysteresis curves of the material Cu10Nb prepared by the present disclosure and the comparative materials pure Ti, Ti6Al4V (TC4), and SUS304 were measured. The specific parameters were as follows: a magnetic field range was ±1.5T, a scanning speed was 1-200 Gauss/s, a magnetic field resolution was 0.02 mT, a temperature control range was 1.9-400 K, a temperature scanning speed was 0.01-12 K/min, and a temperature stability was ±0.2% when it was less than 10 K, and ±0.02% when it was greater than 10 K. Finally, the $\chi$ value of the mass magnetic susceptibility calculated from M=$\chi$/H is shown in Table 4.

TABLE 4

Magnetic susceptibility of processed and comparative materials

| Alloy | Cu10Nb | Ti | TC4 | SUS304 |
|---|---|---|---|---|
| $\chi/10^{-6}$ | 1.26 | 11.29 | 21.31 | 2311.64 |

IV. MRI Test

Firstly, agarose powder with a mass fraction of 2% was added to deionized water and boiled until dissolved. 10 mM Ni(NO$_3$)$_2$ and a 2% agarose solution were fully stirred for mixing to obtain agarose gel. Finally, the mixed gel was poured into a cylindrical open mold with a sample and subjected to still standing for thirty minutes. The agarose gel embedded with the sample was removed and tested under MRI. For the detection of magnetic resonance, fast spin-echo (FSE) and gradient-echo (GRE) pulse sequences were selected for image acquisition. As follows: a long axis of the metal was set parallel and perpendicular to a static magnetic field (B0), and positioning guides were used to achieve the same placement for each MRI test. The magnetic susceptibility of a nickel-doped agarose gel phantom was measured. MR images were acquired using a 1.5 T MR scanner (Signa-HDxt, GE Healthcare Waukesha, USA). T1-weighted sequence spin echo (SE) was used, a frequency matrix was 512 voxels, a phase matrix was 512 voxels, a field of view (FOV) was 150*150 mm, 3 mm multi-layer acquisition without inter-patch gap was conducted, and a total of 3 patches were obtained. The frequency and patch directions were parallel to B0 (head-to-foot, HF). The sequence-specific parameters were as follows: for the SE sequence, a bandwidth (BW) was 16.5 kHz, an echo sequence length was 2, a repetition time (TR) was 400 ms, an echo time (TE) was 11 ms, full Fourier acquisition was conducted, and a number of excitation (NEX) was 1.

Figure 4:
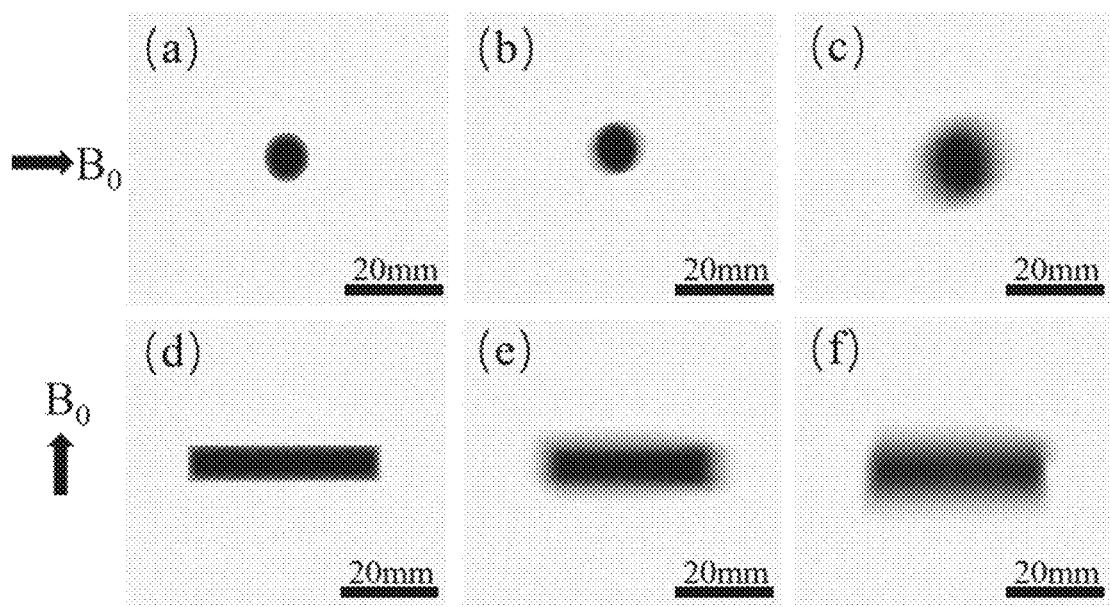
FIG. 4: two-dimensional (2D) artifact maps of MRI in directions parallel to and perpendicular to a magnetic field. a and d are Cu10Nb, b and e are TC4, and c and f are 304 stainless steel.

The test results are shown in FIG. 4. Obviously, the artifact areas of TC4 and SUS304 are larger than that of the Cu10Nb alloy in the directions parallel and perpendicular to the static magnetic field. In addition, an irregular shape is shown.

The above examples are intended to illustrate only the technical conception and characteristics of the present disclosure, and are intended to enable a person familiar with the technology to understand content of the present disclosure and apply the content accordingly, and shall not limit the scope of protection of the present disclosure thereby. Any equivalent change or modification in accordance with the spiritual essence of the present disclosure shall fall within the scope of protection of the present disclosure.

What is claimed is:

1. A copper-niobium alloy for a medical biopsy puncture needle, wherein a needle core and/or needle tube of the puncture needle are/is made of the copper-niobium alloy, and the copper-niobium alloy consists of the following components by mass: 5<Nb≤15 and the balance of Cu.

2. The copper-niobium alloy for a medical biopsy puncture needle according to claim 1, wherein the needle core and the needle tube are processed as follows:
   (1) using granular materials with a purity greater than or equal to 99.99% for smelting to obtain a copper-niobium alloy ingot with a diameter of 60-100 mm;
   (2) cutting off a riser and finishing a surface of the ingot;
   (3) placing the ingot in a high temperature furnace for heat treatment at 900-1,000° C. for 1-2 h, and forging the ingot to a round bar with a diameter of 10-30 mm;
   (4) conducting solution quenching treatment on the round bar at 900-1,000° C. for 2-4 h; and
   (5) conducting needle core forming: drawing the round bar processed in step (4) in multiple passes to the needle core of a design specification, and conducting annealing at 550-650° C. for 1-2 h; and
   conducting needle tube forming: drilling the round bar processed in step (4), and conducting continuous operations of tube reducing, continuous rolling, and heat treatment to finally obtain the needle tube of a design specification.

* * * * *